US00RE40831E

(19) United States
(12) Reissued Patent
Reisner et al.

(10) Patent Number: US RE40,831 E
(45) Date of Reissued Patent: Jul. 7, 2009

(54) HUMAN MONOCLONAL ANTIBODIES TO THE HEPATITIS B SURFACE ANTIGEN

(75) Inventors: Yair Reisner, Old Jaffa (IL); Shlomo Dagan, Rehovot (IL)

(73) Assignee: Yeda Research and Development Co., Ltd., Rehovot (IL)

(21) Appl. No.: 10/423,036

(22) PCT Filed: Jun. 10, 1997

(86) PCT No.: PCT/IL97/00184

§ 371 (c)(1),
(2), (4) Date: Dec. 10, 1998

(87) PCT Pub. No.: WO97/47654

PCT Pub. Date: Dec. 18, 1997

Related U.S. Patent Documents

Reissue of:
(64) Patent No.: 6,254,867
Issued: Jul. 3, 2001
Appl. No.: 09/202,181
Filed: Dec. 10, 1998

(30) Foreign Application Priority Data

Jun. 11, 1996 (IL) ..... 118625

(51) Int. Cl.
*C07K 16/08* (2006.01)

(52) U.S. Cl. ..... 424/149.1; 424/142.1; 424/133.1; 435/5; 435/339; 530/388.15; 530/388.3; 530/388.1

(58) Field of Classification Search ..... 434/133.1, 434/142.1, 149.1; 530/388.15, 388.3, 388.1; 435/5, 339
See application file for complete search history.

(56) References Cited

U.S. PATENT DOCUMENTS

| | | | |
|---|---|---|---|
| 4,883,752 | A | 11/1989 | Eda et al. |
| 5,652,373 | A | 7/1997 | Reisner |
| 5,804,160 | A | 9/1998 | Reisner |
| 5,849,288 | A | 12/1998 | Reisner |
| 5,849,987 | A | 12/1998 | Reisner |
| 5,858,328 | A | 1/1999 | Reisner |
| 5,866,757 | A | 2/1999 | Reisner |

FOREIGN PATENT DOCUMENTS

| | | |
|---|---|---|
| EP | 0179483 | 4/1986 |
| EP | 0438053 | 7/1991 |
| WO | WO9411495 | 5/1994 |
| WO | WO9426784 | 11/1994 |

OTHER PUBLICATIONS

Greenspan et al. (Nature Biotechnology 17: 936–937, 1999).*
Bowie et al (Science, 1990, 257:1306–1310).*
Webster II, 1984, Houghton Mifflin Company, MA, p. 612.*
Ichimori et al., Establishment of hybridomas secreting human monoclonal antibody against tetanus toxin and hepatitis B virus surface antigen, *Biochemical and Biophysical Research Communications,* 129:26–33 (1985).
Ichimori et al., Establishment of hybridomas secreting human monoclonal antibody against tetanus toxin and hepatitis B virus surface antigen, *Biochemical and Biophysical Research Communications,* 142:805–812 (1987).
Marcus et al., Human/Mouse radiation chimera are capable of mounting a human primary humoral response, *Blood,* 86:398–406 (1995).
Lubin et al., Engraftment of human peripheral blood lymphocytes in normal strains of mice, *Blood,* 83:2368–2381 (1994).
Ehrlich et al., Characterization of human monoclonal antibodies directed against hepatitis B surface antigen, *Hum. Antibod. Hybridoma,* 3:2–7 (1992).
Eren et al., Production of specific human monoclonal antibodies to Hepatitis B virus by human lymphocytes engrafted in normal strains of mice, *Journal of Hepatology,* 25:80 (1996).
Denes et al., Natural antibodies do not inhibit xenogeneic transplantation of human PBL in lethally irradiated mice, *Xenotransplantation*, 2:8–18 (1995).
XP0020442g4, Continuous cultures of fused cells secreting antibody of predefined specificity, *Nature,* 256:495–497 (1975).

* cited by examiner

*Primary Examiner*—Robert A Zeman
(74) *Attorney, Agent, or Firm*—Browdy and Neimark, P.L.L.C.

(57) ABSTRACT

Disclosed is a process for obtaining hybridoma cell lines which produce human antibodies capable of binding to the hepatitis B virus surface antigen (HBVsAg), as well as the hybridoma cell lines, and antibodies produced by the cell lines. Also disclosed are various uses of said antibodies in the prevention and treatment of HBV infection. Peripheral blood lymphocytes obtained from human donors having a high titer of anti HBVsAg antibodies are engrafted into normal strains of mice which were lethally irradiated and radioprotected with SCID bone marrow. After immunization of such chimeric mice with HBVsAg, human cells are obtained from the mice spleens and fused in vitro with heteromyeloma cells to generate hybridomas secreting human antibodies having a high affinity and specificity to HBVsAg.

20 Claims, 10 Drawing Sheets

| | | | | | | | | | | | | | | | | | | | |
|---|---|---|---|---|---|---|---|---|---|---|---|---|---|---|---|---|---|---|---|
| | | Ser TCC | Tyr TAT | Val GTG 9 | Leu CTG | Thr ACT | Gln CAG 18 | Pro CCA | Pro CCC | Ser TCG 27 | Val GTG | Ser TCA | Val GTG 36 | Ala GCC | Pro CCA | Gly GGA 45 | Lys AAG | Thr ACG | Ala GCC 54 |
| Arg AGG | Ile ATT | Ser TCC 63 | Cys TGT | Gly GGG | Gly GGA 72 | Asn AAC | Asn AAC | Ile ATT 81 | Gly GGA | Thr ACT | Lys AAA 90 | Asn AAT | Val GTG | His CAC 99 | Trp TGG | Tyr TAC | Gln CAG 108 | Gln CAG | Lys AAG |
| Pro CCA | Gly GGC | Gln CAG 123 | Ala GCC | Pro CCT | Val GTG 132 | Leu CTG | Val GTC | Val GTC 141 | Tyr TAT | Ala GCT | Asp GAT 150 | Ser AGC | Asp GAC | Arg CGG 159 | Pro CCC | Ser TCA | Gly GGG 168 | Ile ATC | Pro CCT |
| Glu GAG | Arg CGA | Phe TTC 183 | Ser TCT | Gly GGC | Ser TCC 192 | Asn AAC | Ser TCT | Gly GGG 201 | Asn AAC | Thr ACG | Ala GCC 210 | Thr ACC | Leu CTG | Thr ACC 219 | Ile ATC | Ser AGC | Arg AGG 228 | Val GTC | Glu GAA |
| Val GTC | Gly GGG | Asp GAT 243 | Glu GAG | Ala GCC | Asp GAC 252 | Tyr TAT | Tyr TAC | Cys TGT 261 | Gln CAG | Val GTG | Trp TGG 270 | Asp GAT | Ser AGT | Val GTT 279 | Ser AGT | Tyr TAT | His CAT 288 | Val GTG | Val GTA |
| Phe TTT | Gly GGC | Gly GGA 303 | Gly GGG | Thr ACC | Thr ACG 312 | Leu CTG | Thr ACC | Val GTC 321 | Leu CTA | Gly GGT | | | | | | | | | |

FIG.10

| | | | | | | | | | | | | | | | | | | | |
|---|---|---|---|---|---|---|---|---|---|---|---|---|---|---|---|---|---|---|---|
| | | Gln CAG | Val GTG | Gln CAG 9 | Leu CTG | Val GTG | Glu GAG 18 | Ser TCT | Gly GGG | Gly GGA 27 | Gly GGC | Val GTG | Val GTC 36 | Gln CAG | Pro CCT | Gly GGG 45 | Gly GGG | Ser TCC | Leu CTG 54 |
| Arg AGA | Leu CTC | Ser TCC 63 | Cys TGT | Ala GCA | Pro CCG 72 | Ser TCT | Gly GGA | Phe TTC 81 | Val GTC | Phe TTC | Arg AGG 90 | Ser AGT | Tyr TAT | Gly GGC 99 | Met ATG | His CAC | Trp TGG 108 | Val GTC | Arg CGC |
| Gln CAG | Thr ACT | Pro CCA 123 | Gly GGC | Lys AAG | Gly GGG 132 | Leu CTT | Glu GAG | Trp TGG 141 | Val GTG | Ser TCA | Leu CTT 150 | Ile ATA | Trp TGG | His CAT 159 | Asp GAT | Gly GGA | Ser AGT 168 | Asn AAT | Arg AGA |
| Phe TTC | Tyr TAT | Ala GCA 183 | Asp GAC | Ser TCC | Val GTG 192 | Lys AAG | Gly GGC | Arg CGA 201 | Phe TTC | Thr ACC | Ile ATC 210 | Ser TCC | Arg AGA | Asp GAC 219 | Asn AAT | Ser TCC | Lys AAG 228 | Asn AAC | Thr ACA |
| Leu TTG | Tyr TAT | Leu TTG 243 | Gln CAA | Met ATG | Asn AAC 252 | Ser AGC | Leu CTG | Arg AGA 261 | Ala GCC | Glu GAA | Asp GAC 270 | Thr ACG | Ala GCT | Met ATG 279 | Tyr TAC | Phe TTC | Cys TGT 288 | Ala GCG | Arg AGA |
| Glu GAG | Arg AGG | Leu CTG 303 | Ile ATT | Ala GCA | Ala GCA 312 | Pro CCT | Ala GCT | Ala GCC 321 | Phe TTT | Asp GAC | Leu CTC 330 | Trp TGG | Gly GGC | Gln CAG 339 | Gly GGA | Thr ACC | Leu CTG 348 | Val GTC | Thr ACC |
| Val GTC | Ser TCC | Ser TCG 363 | | | | | | | | | | | | | | | | | |

FIG.11

HUMAN MONOCLONAL ANTIBODIES TO THE HEPATITIS B SURFACE ANTIGEN

Matter enclosed in heavy brackets [ ] appears in the original patent but forms no part of this reissue specification; matter printed in italics indicates the additions made by reissue.

FIELD OF THE INVENTION

The present invention concerns a process for obtaining hybridoma cell lines which produce human antibodies capable of binding to the hepatitis B virus surface antigen, the hybridoma cell lines, antibodies produced by the cell lines, and various uses thereof.

BACKGROUND OF THE INVENTION

Hepatitis B virus (HBV) infection is a major worldwide health problem. Approximately 5% of the world population is infected by HBV and chronically infected patients carry a high risk of developing cirrhosis and hepatocellular carcinoma. (Progress in Hepatitis Research: Hepatitis B virus (HBV), Hepatitis C virus (HCV) and Hepatitis Delta virus (HDV) Ed. O. Crivelli, Sorin Biomedica, 1991).

The immune response to HBV-encoded antigens includes both a cellular immune response which is active in the elimination of HBV infected cells, as well as a humoral antibody response to viral envelope antigens which contributes to the clearance of circulating virus particles. The dominant cause of viral persistence during HBV infection is the development of a weak antiviral immune response.

Recombinant HBV vaccines provide a safe and effective means for active immunization against HBV, however, they do not always induce a sufficient and rapid antibody response.

Interferon-α has been used in the therapy of Hepatitis B infection shown an efficacy of only 30–40% in highly selected patients.

In addition, passive immunization with human polyclonal anti Hepatitis B antisera has been shown to be effective in delaying and even preventing recurrent HBV infection (Wright, T. L. and Lau, J. Y. N. The Lancet 342:1340–1344, (1993)). Such human polyclonal antisera are prepared from pooled plasma of immunized donors. These preparations are very expensive and available in relatively small amounts. Furthermore, pooled plasma may contain contaminated blood samples and thus treatment with such antisera increases the patient's risk to contract other viral infections such as hepatitis C or HIV.

An alternative approach for the treatment of HBV infection is the use of monoclonal antibodies (MoAb).

PCT patent application PCT/NL94/00102 discloses human monoclonal antibodies directed against Hepatitis B surface antigen HBVsAg which are secreted by the hybridoma cell lines Mab 4–7B and Mab 9H9. The monoclonal antibody secreted by the cell line Mab 4–7B recognizes a linear epitope of HBVsAg and is different from the Mab 9H9 monoclonal antibody which recognizes a conformational epitope. The antibodies are claimed for simultaneous use in the treatment of chronic Hepatitis B infections.

PCT patent application PCT/US92/09749 discloses human monoclonal antibodies against HBVsAg which are secreted by the hybridoma cell lines PE1-1, ZM1-1, ZM1-2, MD3-4 and LO3-3. The antibodies bind to different HBV epitopes and are used for reducing the level of circulating HBVsAg.

Japanese Patent Application JP 93066104 discloses a hybridoma of a human lymphocyte cell strain TAW-925 and a human lymphocyte transformed by Epstein-Barr virus. The hybridoma produces a human monoclonal antibody against HBVsAg.

U.S. patent application Ser. No. 4,883,752 discloses preparation of human-derived monoclonal antibody to HBVsAg, by administration of HBVsAg vaccine to humans, recovering their lymphocytes, stimulating the lymphocytes in vitro by a non specific stimulator, fusing said cells with a myeloma cell, and selecting for hybridomas with secrete anti HBVsAg antibodies.

Ichimori et al, Biochem. and Biophysic. Research Communications 129(1):26–33, 1985 discloses a hybridoma secreting human anti HBVsAg monoclonal antibodies which recognize the a-determinant of HBVsAg. Later, Ichimori, et al., supra 142(3):805–812, 1987 disclosed another hybridoma which stably secretes human monoclonal antibody against HbsAg.

The abovementioned antibodies were all developer by in vitro immortalization of antibody-producing cells from individuals positive for anti-HBV antibodies.

A new approach enabling adaptive transfer of human peripheral blood mononuclear cells (PBMC) into lethally irradiated normal strains of mice radioprotected with severe combined immune deficiency (SCID) bone marrow was recently described (Lubin I., et al., Blood, 83:2368, 1994). Secondary humoral responses to various recall antigens as well as a primary humoral response to other antigens were shown to be generated effectively in such human/mouse chimeras (Marcus H., et al, Blood 86:398–406, 1995).

SUMMARY OF THE INVENTION

In accordance with the present invention, it was found that hybridoma cell lines secreting human antibodies capable of binding to the Hepatitis B surface antigen (HBVsAg) may be obtained using the above mentioned human/mouse chimeras. In accordance with the present invention, human peripheral blood lymphocytes (PBL) from human donors positive for anti HBVsAg antibodies are engrafted into normal strains of mice which were lethally irritated and radioprotected wits SCID bone marrow. After immunization of such chimeric mice with HBVsAg, human cells are obtained from the mice spleens and fused in vitro with heteromyeloma cells to generate hybridomas secreting human antibodies having a high affinity and specificity to HBVsAg.

The present invention thus provides a process for obtaining human monoclonal antibodies (hMoAb) capable of binding to Hepatitis B virus surface antigen (HBVsAg) comprising:

(a) immunizing a chimeric rodent M4 having xenogeneic hematopoietic cells with Hepatitis B surface antigen (HBVsAg) such that xenogeneic antibody-producing cells are produced in said rodent, wherein said rodent M4 is a rodent M1, the hematopoietic cells of which have been substantially destroyed, said rodent M1 having transplanted therein hematopoietic cells derived from a mouse M2 having a hematopoietic deficiency, and xenogeneic hematopoietic cells derived from human M3;

(b) removing and immortalizing said antibody-producing cells;

(c) selecting and cloning the immortalized antibody producing cells producing the antibodies capable of binding to HBVsAg and;

(d) isolating the antibodies produced by the selected, cloned immortalized antibody producing cells.

In accordance with the invention, spleens of the immunized chimeric rodent M4 are removed between 12 and 20 days after human PBL transplantation, preferably at day 14 after transplantation thereof. Cell suspensions are prepared prepared from the spleens and the antibody producing cells obtained from the immunized [a heteromyeloma by techniques well known in the art (e.g. Kohler & Milstein,] chimeric rodent M4 are fused preferably with a human-mouse fusion partner such as a heteromyeloma by techniques well known in the art (e.g., Kohler & Milstein, Nature, 256:495–497, 1975). In order to isolate the antibodies produced by the selected hybridoma cell lines in accordance with the invention, the hybridoma cell lines are either cultured in vitro in a suitable medium wherein the desired monoclonal antibody is recovered from the supernatant or, alternatively, the hybridoma cell lines may be injected intraperitoneally into mice and the antibodies harvested from the malignant ascitis or serum of these mice. The supernatant of the hybridoma cell lines are first screened for production of human IgG antibodies by any of the methods known in the art such as enzyme linked (RIA). Hybridomas testing positive for human IgG are then further screened for production of anti HBVsAg antibodies by their capability to bind to HBVsAg.

The M1 rodent in accordance with the invention is preferably a rodent conventionally used as a laboratory animal, most preferably a rat or a mouse.

The mouse M2 may have any hematopoietic deficiency including genetic hematopoietic deficiencies as well as induced hematopoietic deficiencies. Non limiting examples of hematopoietic deficiencies include SCID, Bg, Nu, Xid or mice having any combination of the abovementioned hematopoietic deficiencies. In addition, the hematopoietic deficiency may also be a result of gene deletion or transgenic mice may be used.

The hematopoietic cells derived from the donor mouse M2 are preferably bone marrow cells either untreated or depleted of T cells. Other suitable sources of hematopoietic cells which may also be used include, for example, spleen cells, fetal liver cells or peripheral blood cells.

The xenogeneic hematopoietic cells derived from the human M3 are preferably PBL cells but may also be derived from any suitable source of human hematopoietic cells such as bone marrow cells, cord blood cells, thymus spleen or lymphnode cells, etc.

By a most preferred embodiment, the rodent M1 is a mouse or rat, the mouse M2 is a SCID mouse and the xenogeneic hematopoietic cells derived from the human M3 are PBLs from a human M3 which has already been exposed to the HBVsAg either spontaneously as a result of a prior infection or induced following vaccinations. Such humans will have a relatively high titer of anti HBVsAg antibodies as compared to individuals which have never been infected with HBV and, therefore, when PBLs from such donors are used as M3 donor cells in accordance with the present invention, the immunization of the M4 chimeric mouse with HBVsAg will elicit a secondary immune response of the transplanted human PBLs in the M4 chimeric mouse. A most preferred human donor M3 is such which tested negative for the HB virus but shows a high titer of antibodies against HBVsAg. Such PBLs from the human M3 donor may be obtained either by whole blood donation or by leukophoresis.

The HBVsAg used for immunizing the chimeric rodent M4 in accordance with the invention is preferably a Hepatitis B virus vaccine containing the purified major surface antigen of the virus prepared by recombinant DNA technology and formulated as a suspension of the major surface antigen adsorbed on aluminum hydroxide (ENGERIX B, SIB Biological (Rixensart, Belgium)).

The present invention is also directed to hybridoma cell lines producing human monoclonal antibodies capable of binding to HBVsAg, as well as to human monoclonal antibodies capable of binding to HBVsAg and fragments thereof substantially maintaining the antigen binding characteristics of the whole antibody. Such fragments may be, for example, Fab or $F(ab)_2$ fragments obtained by digestion of the whole antibody with various enzymes as known and described extensively in the art. The antigenic characteristics of an antibody are determined by testing the binding of an antibody to a certain antigenic determinant using standard assays such as RIA, ELISA or FACS analysis.

Typically, the human monoclonal antibodies obtained by the method of the present invention have a relatively high affinity to HBVsAg being in the range of about $10^{-9}$ M to about $10^{-10}$ M as determined in a competative ELISA assay.

In accordance with a specific embodiment of the present invention there are provided hybridoma cell lines designated herein as "18.5.1013" and "19.79.5" which were deposited on May 22, 1996, in the European Collection of Cell Cultures (ECACC, CAMR, Salisbury, Wiltshire, SP40JG, U.K.) under Accession Nos. 96052170 and 96052168, respectively. Anti HBVsAg human monoclonal antibodies secreted by the above hybridoma cell lines and designated herein as "Ab18.5.1013" and "Ab19.79.5", respectively, are also provided as well as fragments thereof retaining the antigen binding characteristics of the antibodies, and antibodies capable of binding to the antigenic epitope bound by "Ab18.5.1013" and "Ab19.79.5".

The antigen bound by the antibodies defined above also constitutes an aspect of the invention.

Further aspects of the present invention are various diagnostic, prophylactic and therapeutic uses of the human anti HBVsAg monoclonal antibodies and the Ag bound by them. In accordance with this aspect of the invention, pharmaceutical compositions comprising the human anti HBVsAg monoclonal antibodies may be used for the treatment of chronic Hepatitis B patients by administering to such a patient a therapeutically effective amount of the monoclonal antibody or portion thereof capable of binding to the HBVsAg being an amount effective in alleviating the symptoms of the HBV infection or reducing the number of circulating viral particles in an individual.

Such pharmaceutical compositions may comprise one or more antibodies of the invention. In addition to the antibodies of the invention the pharmaceutical Compositions may optionally also comprise a carrier selected from any of the carriers known in the art. One example of such a carrier is a liposome. The pharmaceutical compositions of the invention may also comprise various diluents and adjuvants known per se.

The compositions of the invention may be administered by a variety of administration modes including parenterally, orally etc.

Compositions comprising the antibodies of the invention, as described above, may be administered in combination with other anti viral agents. Such agents may include, as a non limiting example: Interferons, anti [Hepatitus HB] Hepatitis B (HB) monoclonal antibodies, anti HB polyclonal antibodies, nucleoside analogs, and inhibitors of DNA polymerase. In the case of such a combination therapy the antibodies may be given simultaneously with the anti viral agent or sequentially either before or after treatment with the anti viral agent.

The pharmaceutical compositions of the invention may also be used, for example, for immunization of new born babies against HBV infections or for immunization of liver transplantation patients to eliminate possible recurrent HBV infections in such patients.

By a further embodiment, the antibodies of the invention may also be used in a method for the diagnosis of HBV infections in an individual by obtaining a body fluid sample from the tested individual which may be a blood sample, a lymph sample or any other body fluid sample and contacting the body fluid sample with a human and HBVsAG antibody of the invention under conditions enabling the formation of antibody-antigen complexes. The level of such complexes is then determined by methods known in the art, a level significantly higher than that formed in a control sample indicating an HV infection in the tested individual. In the same manner, the specific antigen bound by the antibodies of the invention may also be used for diagnosis. In the same manner, the specific antigen of the invention may also be used for diagnosis of HBV infection in an individual by contacting a body fluid sample with the Ag and determining the presence of Ag-Ab complexes in the sample as described above. In addition, the Ag of the invention may be used for immunizing an individual to elicit a humoral response against HBV.

The present invention further provides a kit for use in the therapy of HB infections or diagnosis of such infections comprising the antibodies of the invention, the antigen bound by the antibodies of the invention and any further reagents necessary for detecting such antibodies or antigens in a tested sample.

PBL+Alum: the chimeric mice were further transplanted with human PBL from donors positive for anti HBs antibodies, and vaccinated with Alum alone (no ENGERIX B).

SCID–BM+ENGERIX: the chimeric mice were vaccinated with ENGERIX B (no transplantation of human PBL).

SCID–BM+Alum: the chimeric mice were vaccinated with Alum (no human PBL and no ENGERIX B).

The black line represents the initial level of anti HBs antibodies in the serum of the human PBL donor.

Figure 2:
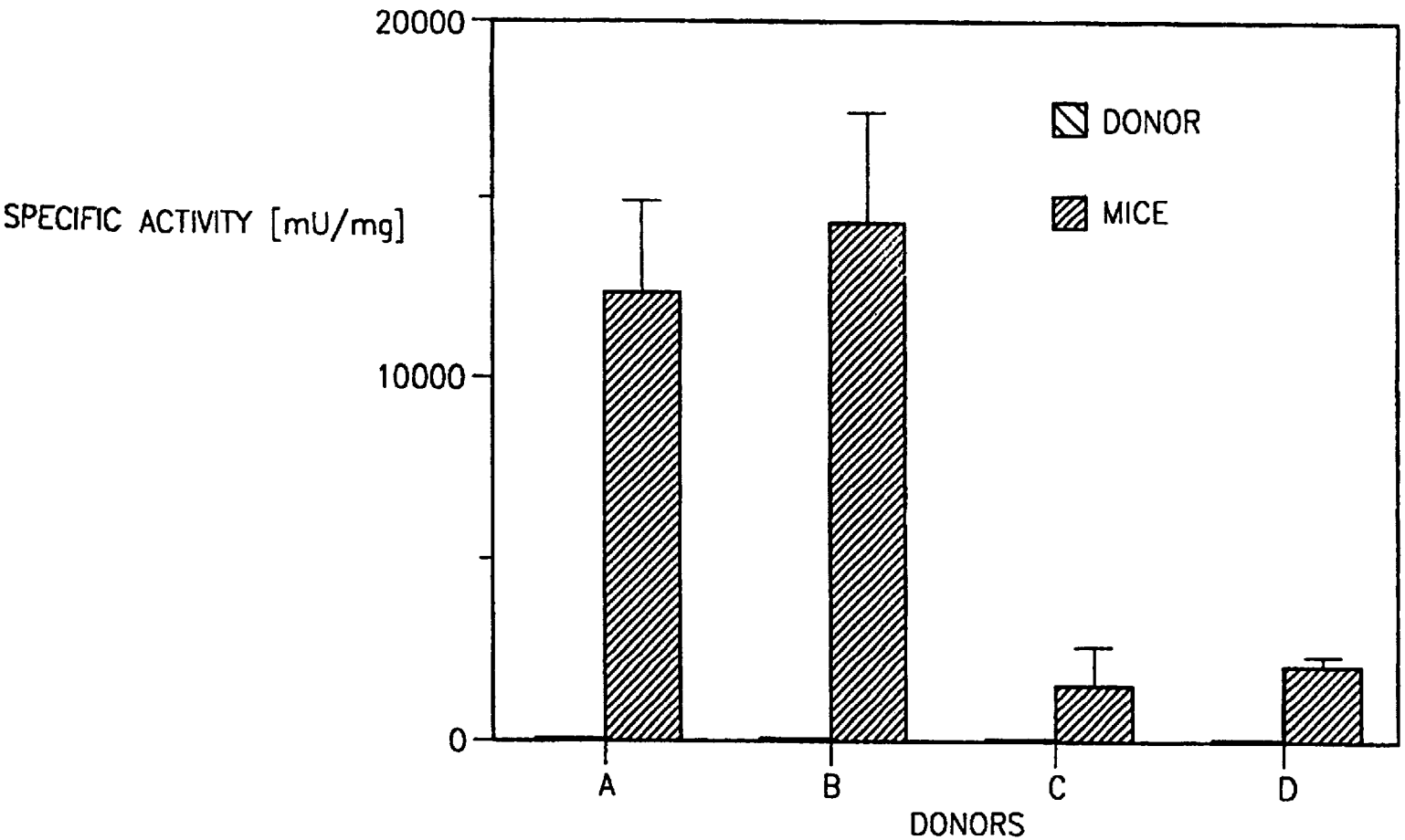

FIG. 2 is a graphic representation showing the specific activity, i.e. the levels of anti HBVs antibodies per mg of human Ig in the sera of human donors (A–D, black columns) and the specific activity in the sera of chimeric mice transplanted respectively with human PBL of said donors (A–D, striped columns).

Figure 3:
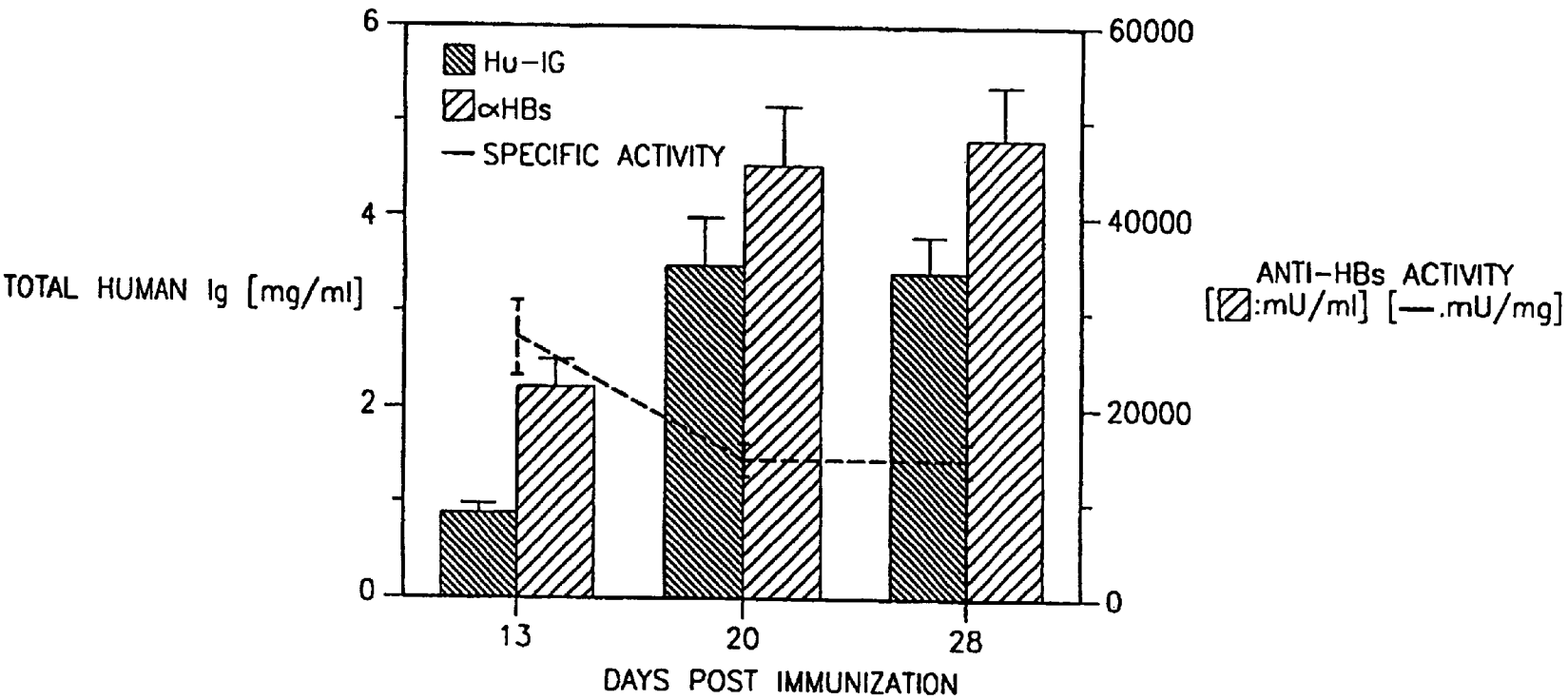

FIG. 3 is a graphic representation showing time response curve of anti HBs antibodies specific activity (mU/mg) in sera of chimeric mice (dotted line). The black columns represent the level of total human Ig (mg/ml), and the striped columns represent the level of specific anti HBs antibodies (mU/mi).

Figure 4:
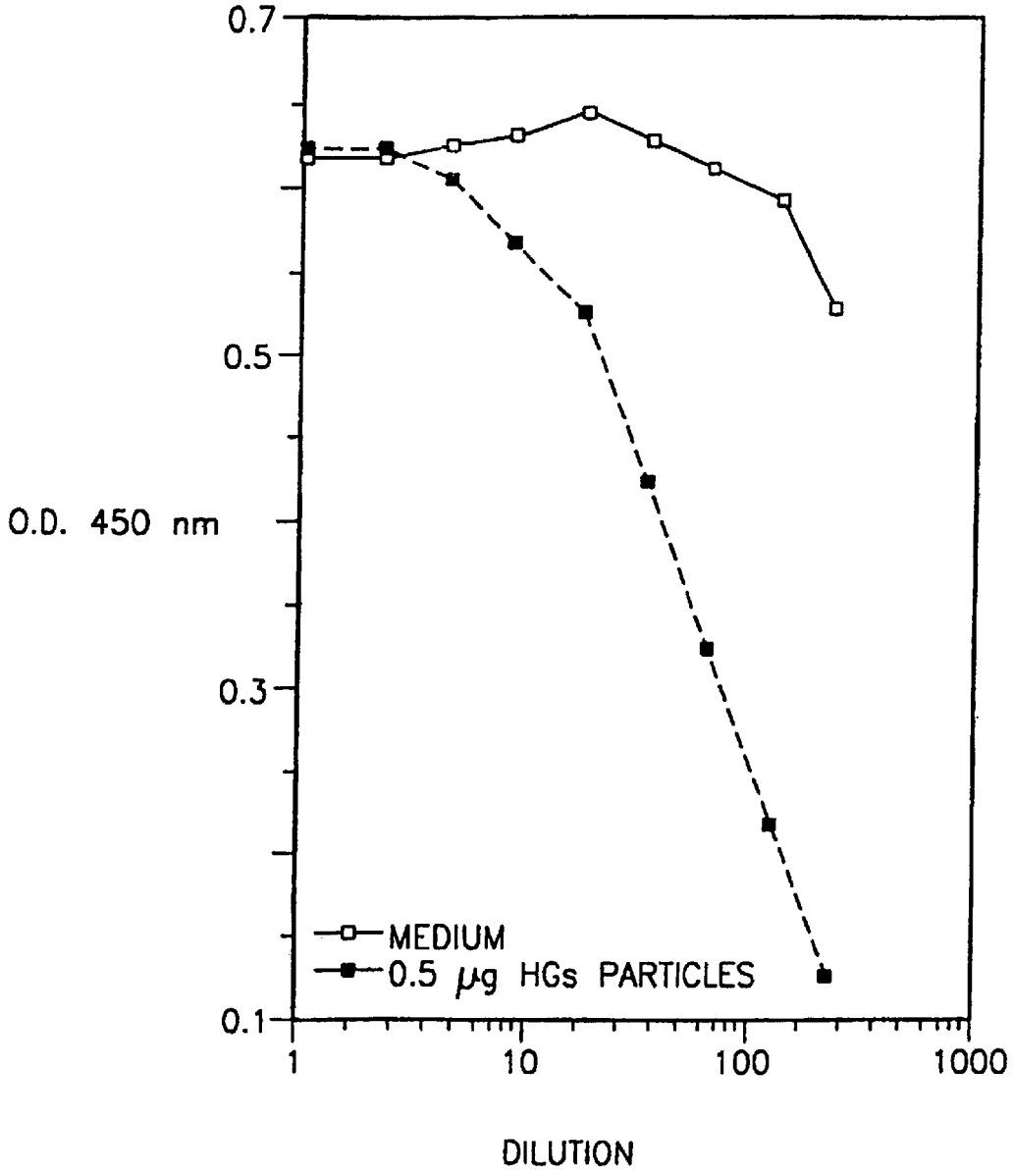

FIG. 4 is a graphic representation showing competitive inhibition of binding of anti HBs antibodies to HBs particles. The extent of binding was measured by ELISA using a horseradish peroxidase labeled anti human IgG secondary antibody. The anti HBs antibodies were diluted as indicated in the graph in medium (empty squares) or in 0.5 μg/ml HBs particles (black squares).

Figure 5:
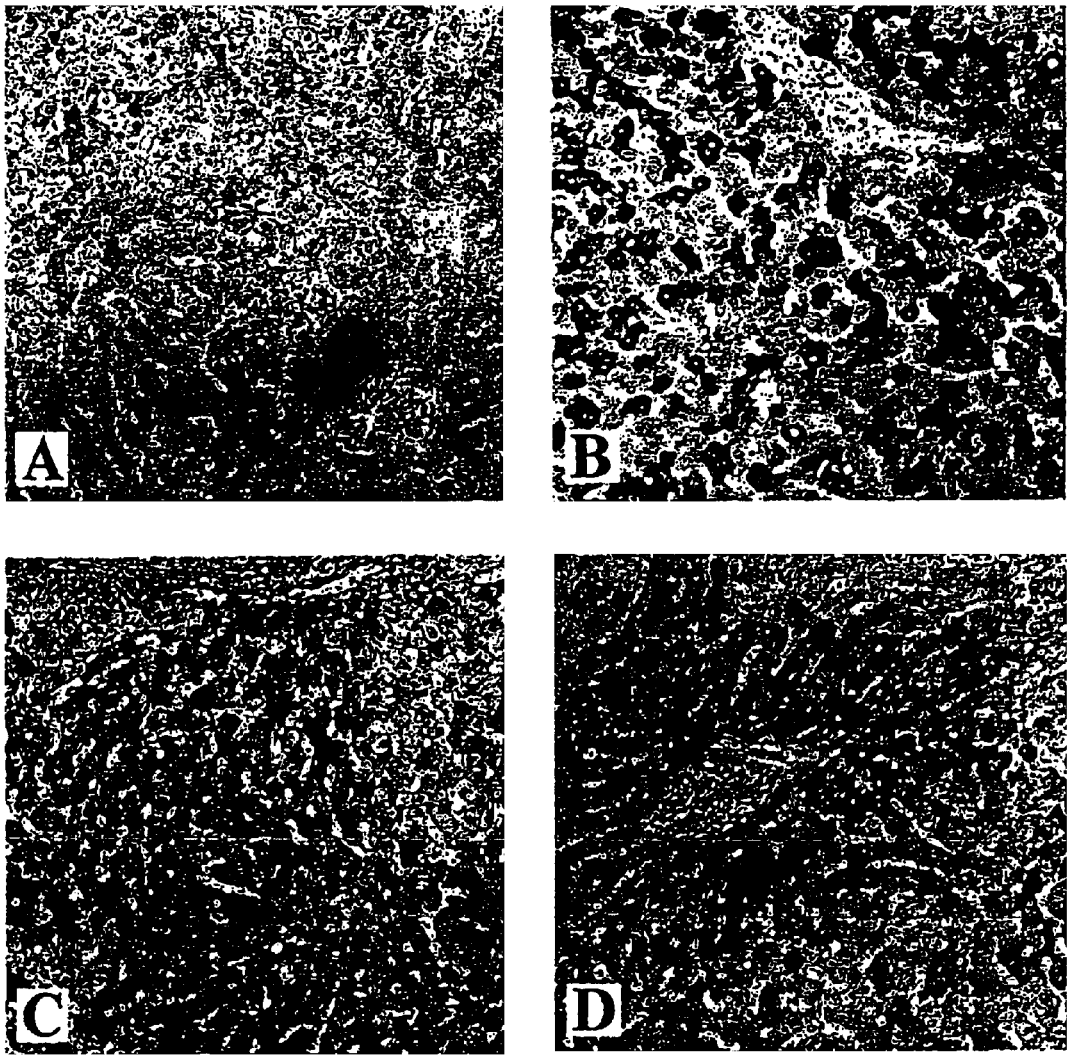

FIG. 5 is a photograph showing Hepatitis B infected liver sections stained with anti HBVs antibodies. All sections were stained with a "secondary" antibody, i.e. goat anti human Ig conjugated to biotin.

A—negative control. No first antibody.

B—positive control. First antibody-mouse anti HB antibody and a secondary anti-mouse Ig.

C—staining with anti HBs antibody No. 19.79.5.

D—staining with anti HBs antibody No. 18.5.1013.

Reference will now be made to the following Examples which are provided by way of illustration and are not intended to be limiting to the present invention.

Figure 6:
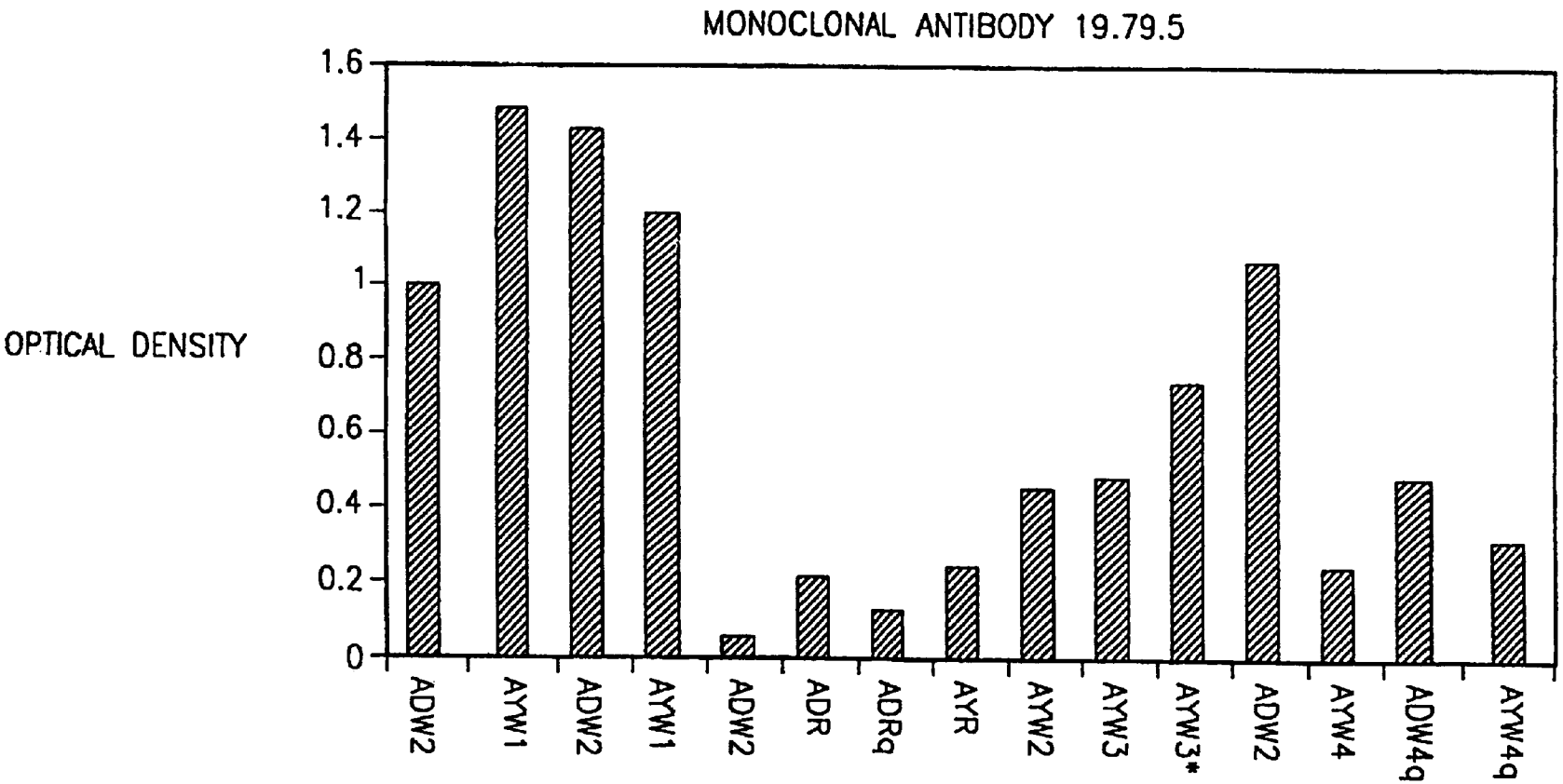

FIG. 6 is a schematic representation of the binding of Ab 19.79.5 to a set of 15 well characterized HBsAg types. The y axis represents optical density units. The x axis represents different HBsAg types.

Figure 7:
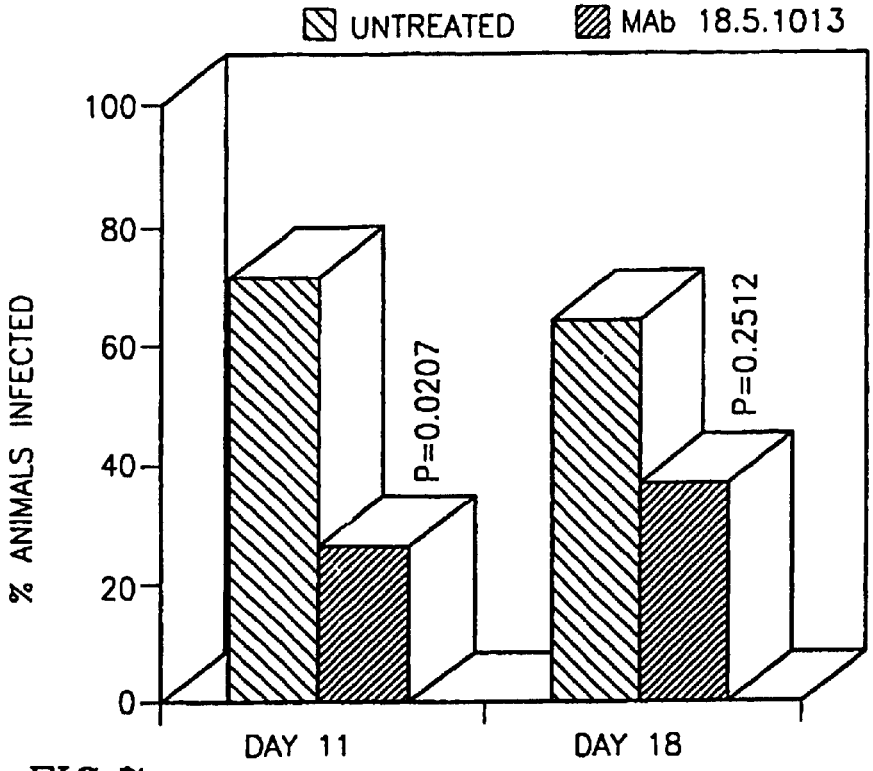

FIG. 7 is a graphic representation of the percentage of HBV infected animals at days 11 and 18 in the untreated group and Ab 18.5.1013 treated group (in the inhibition model).

Figure 8:
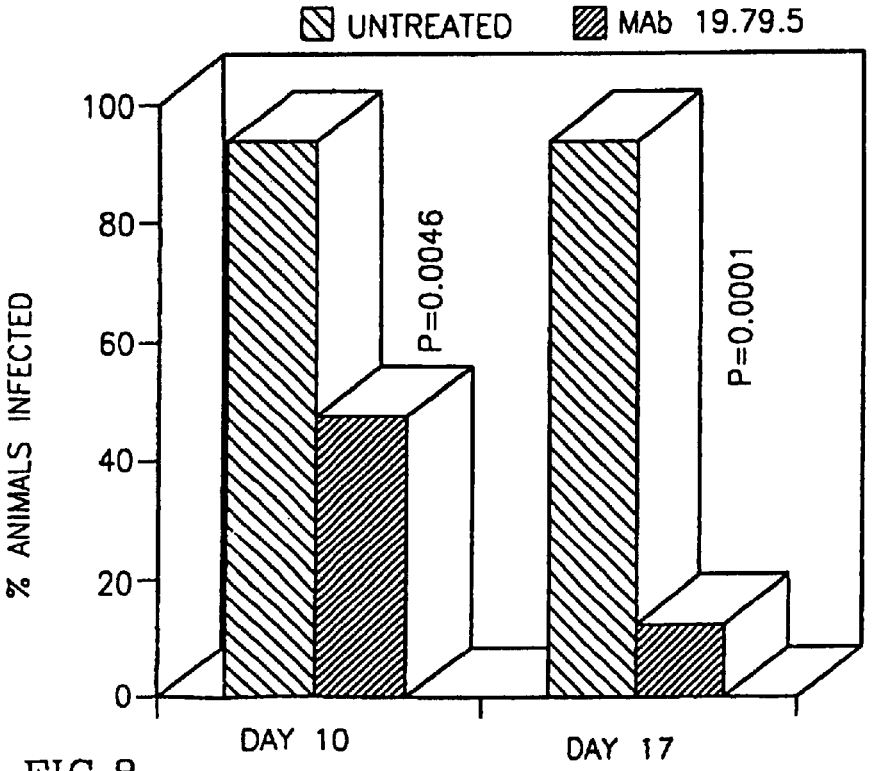

FIG. 8 is a graphic representation of the percentage of HBV infected animals at days 10 and 17 in the untreated group and Ab 19.79.5 treated group (in the combined prophylaxis/inhibition model).

Figure 9:
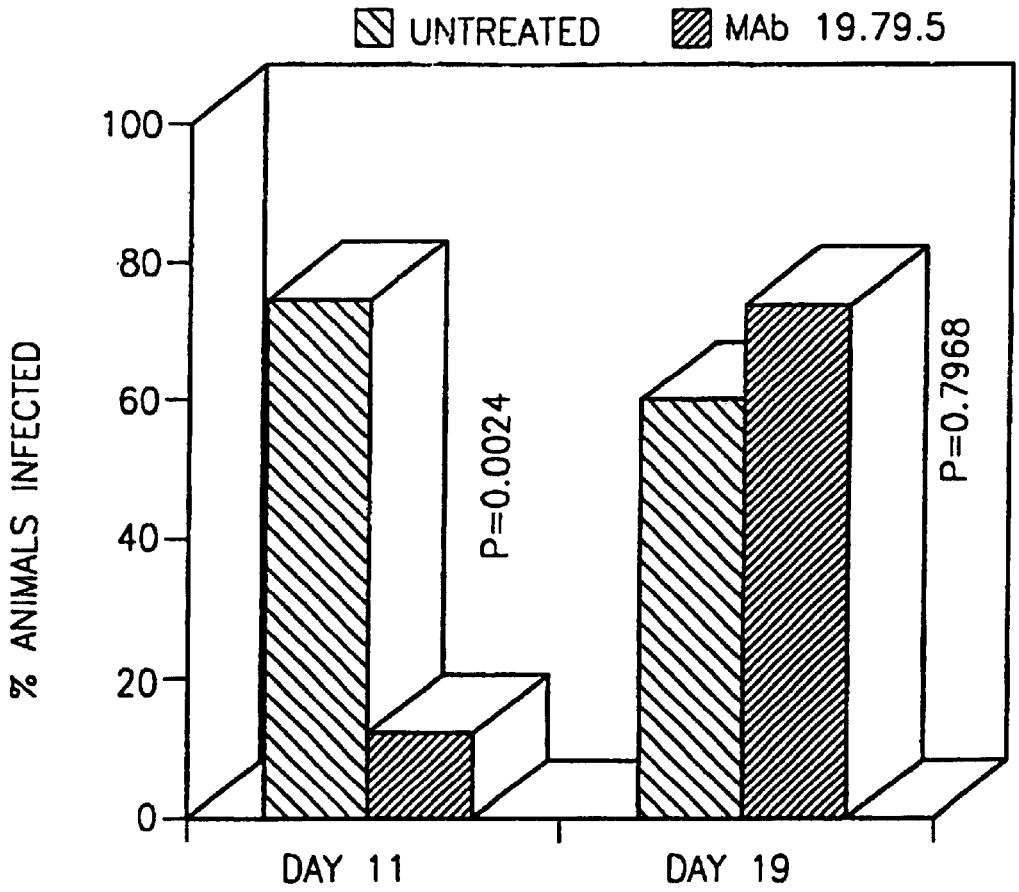

FIG. 9 is a graphic representation of the percentage of HBV infected animals at days 11 and 19 in the untreated group and Ab 19.79.5 treated group (in the combined inhibition/treatment model).

FIG. 10 Nucleic acid sequence (SEQ ID NO:1) and corresponding amino acid sequence (SEQ ID NO:2) of the light chain of the variable domain of Ab 19.79.5.

FIG. 11 Nucleic acid sequence (SEQ ID NO:3) and corresponding amino acid sequence (SEQ ID NO:4) of the heavy chain of the variable domain of Ab 19.79.5.

EXAMPLES

Materials and Methods

Mice:

Animals used were 6–10 weeks old. BALB/c mice were obtained from Harlan (Weizmann Institute Animal Breeding Center (Rehovot, Israel)), SCID/NOD mice from the Weizmann Institute Animal Breeding Center (Rehovot, Israel). All mice were fed sterile food and acid water containing cyprofloxacin (20 μg/ml) (Bayer, Leverkusen, Germany). Whenever necessary, mice were injected daily with 1 mg Fortum i.p. for five days post BMT (Glaxo Operations UK, Greenford, England).

Conditioning Regimens:

BALB/c mice were exposed to total body irradiation (TBI), from a gamma beam 150-A 60Co source (produced by the Atomic Energy of Canada, Kanata, Ontario) with F.S.D of 75 cm and a dose rate of 0.7 Gy/min, with 4 Gy followed 3 days later by 10–11 Gy (split dose).

Preparation and Transplantation of Bone Marrow Cells:

The femoral and tibial bones were removed from mice and homogenized in a sterilized 50 ml Omni-Mixer stainless steel chamber (Omni-Mixer Hmogenizer, Model No. 17106, OMNI International, Waterbury, Conn. USA).

Recipient mice were injected i.v. with $4–6\times10^6$ of SCID/NOD bone marrow cells (in 0.2 ml PBS) immediately after irradiation.

Transplantation of Peripheral Blood Lymphocytes:

Peripheral blood lymphocytes (PBL) were obtained after informed consent by leukophoresis from donors positive for HBs antibodies and negative for HBV. PBLs were washed twice, counted and resuspended in PBS to the desired cell concentration.

$100\times10^6$ human PBL were injected intraperitoneally (i.p.) into recipient mice, conditioned as described above. Control mice did not receive human PBL.

Immunization of the Chimeric Animals:

Mice were immunized once with hepatitis B vaccine (ENGERIX-B; SB Biologicals Rixensart, Belgium) administered i.p. together with the PBL.

Cell and Plasma Collection from Human Mouse Chimera:

Animals were bled from the retro-orbital vein using heparin-coated glass capillaries. Plasma was kept for human-Ig determination. Spleens were removed after the animals were sacrificed by cervical dislocation, cut into pieces and pressed through stainless steel sieves to make a cell suspension in PBS.

Cell Fusion:

Cells were mixed with the human-mouse heteromyeloma HMMA2.11TG/0 (Posner et al. Hybridoma, 6:611–625, 1987) at 3:1 ratio. Fusion was performed with 50% (w/v) PEG 1500 (Boehringer Manheim GmbH) in a concentration of 3000 cells/well in 96-well U-bottom microtiter plates (Nunc, Denmark) in complete medium containing HAT-supplement (1x) (Biological Industries, Beit Haemek, Israel). Cells were fed with fresh HAT-medium a week latter. Two weeks after fusion supernatants were harvested for ELISA and medium was replaced with fresh HT-medium.

Hybridoma cultures secreting specific anti-HBs Ig were cloned at 0.5 cell/well in 96-well U-bottom microtiter plates.

Determination of Human Immunoglobulin:

Sera were tested for antigen specific and total human Ig. Total human Ig was quantified by sandwich ELISA using goat F(ab)2-purified anti-human IgG+IgM+IgA (Zymed Laboratories, San Francisco, Calif.) as the capture agent and peroxidase-conjugated purified goat anti-human (Zymed Laboratories) as the detection reagent. Human serum of known immunoglobulin concentration was used as the standard (Sigma, Rehovot,Israel). Microplates (Nunc, Roskilde, Denmark) pre-coated with the capture reagent (2.5 ug/ml, 50 ul/well) and blocked with 1% BSA were incubated overnight at 4C with dilutions of plasma from 1:20000 to 1:640000, or the standard from 0.2 to 0.06 ug/ml, then washed 5 times with PBS-Tween solution. The detection reagent was added and the plates were incubated for 1 h at 37 C, then washed again 3 times. Fresh substrate solution (TMB, Sigma) was added and, after peroxidase-catalyzed color development, the reaction was stopped by addition of 10% sulfuric acid. Absorbance at 450 nm was quantified on an ELISA reader (Dynatech, Port Guernsey, Channel Islands, UK).

Concentration of antigen-specific human antibodies in mice sera was determined by HBsAb EIA kit (ZER, Jerusalem, Israel).

Human antibodies in hybridoma supernatants were determined by overnight incubation of supernatants on goat anti-human IgG+A+M (Zymed) coated plates, with goat anti-human IgG-peroxidase conjugated as the secondary reagent.

Antigen-specific antibodies in hybridoma supernatants were determined as above using Hbs antigen coated plates.

Determination of Human IgG Subclasses:

Human IgG subclasses were determined by sandwich ELISA using goat F(ab)2-purified anti-human IgG+IgM+IgA (Zymed Laboratories, San Francisco, Calif.) coated plates and Hbs antigen coated plates. Mouse anti-human IgG subclasses (Sigma) were used as second antibody and peroxidase-conjugated purified goat anti-human (Zymed Laboratories) as the detection reagent.

Statistic Analysis:

Statistical analysis was performed using the STAT VIEW II program (Abacus Concepts, Inc., Berkeley, CA) on a Mackintosh Quadra 605 or Microsoft EXCEL 5.0 (Microsoft) on a 486 DX2 PC compatible. Student t-test, Anova correlation and regression analysis were utilized to calculate probability (p) and correlation coefficient (r) values. Results are presented as mean±standard error.

Affinity Constant Measurements:

Determination of affinity constants (KD) of the different anti-HBs antibodies to ad antigen (Chemicon Cat. No. AG 850) in solution were performed according to Friguet et al. (Journal of Immunological Methods, 77:305–319, 1985). The antigen at various concentrations ($3.5\times10^{-10}$M to $1.4\times10^{-9}$M) was first incubated in solution with a constant amount of antibody ($3.4\times10^{-11}$M), in 0.1 M sodium phosphate buffer containing 2 mM EDTA and 10 mg/ml BSA, pH 7.8 (medium buffer). After overnight incubation at 20 C the concentration of free antibody was determined by an indirect ELISA. A volume of 300 ul of each mixture were transferred and incubated for 2 h at 20 C into the wells of a microtiteration plate (Nunc) previously coated with Ad (50 μl/well at 1 μg/ml in 0.1 M $NaHCO_3$ buffer, pH 9.6 for 2 h at 37° C.). After washing with PBS containing 0.04% TWEEN 20, (polyoxythylene sorbitan monolaurate) the bound antibodies were detected by adding HRP-$F(ab')_2$ Goat anti human IgG (Zymed) diluted 1:3000 with medium buffer, 50 μl/well 2 h at 20° C. The plate was developed with TMB chromogen (Sigma T-3405 tablets) 50 μl/well, the reaction stopped with 10% $H_2SO_4$ 50 μl/well and the plate read in an ELISA reader at 450 nm. The conditions were chosen so that the resulting f values (see Friguet et al.) were around 0.1. The antibody concentration used was deduced from an ELISA calibration done on the same plate. The affinity constant KD was calculated from the relevant Scatchard plot.

Inhibition Assays:

The inhibition assay was performed in microtiter plates coated with HBs particles (2 μg/ml in PBS). The plate was blocked with 3% BSA in PBS.

Hybridoma supernatants containing anti HBs antibodies were serially diluted. 50 μl of each dilution were added to the coated microtiter wells. Subsequently, 50 μl of HBs particles (ad/ay, 0.5 μl/ml in PBS) or PBS alone were added to each well. The plates were incubated overnight at room temperature in a humid chamber and washed 5 times with PBS-Tween. Next, 50 μl of goat anti human IgG conjugated to HRP (diluted 1:5000 in PBS) were added to each well. After a 4 hour incubation at room temperature in a humid chamber the plates were washed 5 times with PBS-Tween, and TMB was added to each well. Results were read using an ELISA reader, in a wavelength of 450 nm.

Immunohistostaining:

HBV positive liver fragment was fixed in 4% neutral buffered formaldehyde for 24 h and then embedded in paraffin using routine procedures. Sections of 4 μm thickness were cut from paraffin blocks and mounted on polylysine-coated slides. After deparaffinization and peroxidase quenching staining was performed using our monoclonal Human anti-HBs Protein A-purified antibodies followed by biotinylated Goat anti-Human IgG (H+L) (Zymed, San Francisco, Calif.) usig Histostain-SPTM kit (Zymed) according to the manufacture's recommendation. Control slides without using the 1st Human anti-HBs antibody were stained in parallel.

Sequence analysis:

Total RNA was isolated from $10\times10^6$ hybridoma cells with RNAsol B reagent (TEL-TEX, Inc. Friendswood, Tex.). cDNA was prepared from 10 μg of total RNA with reverse transcriptase and oligo dT (Promega, Madison, Wis.) according to standard procedures. PCR was performed on 1/50 of the RT reaction mixture with $V_H$, $V_\lambda$, or [Vτ5'] Vκ5'leader primers and 3' primers corresponding to human constant region. The PCR fragments were cloned into pGEM-T vector (Promega). The inserts were sequenced using an ABI 377 sequencing machine. Sequences were analyzed by comparison to Genbank and by alignment to Kabat sequences (Kabat et al. 1991, Sequences of proteins of immunological interest ($5^{th}$ Ed.) U.S. Dept. of Health and Human Services, National Institutes of Health, Bethesda, Md.).

Example 1

Production of Human anti HBs Antibodies in Chimeric Mice

Figure 1:
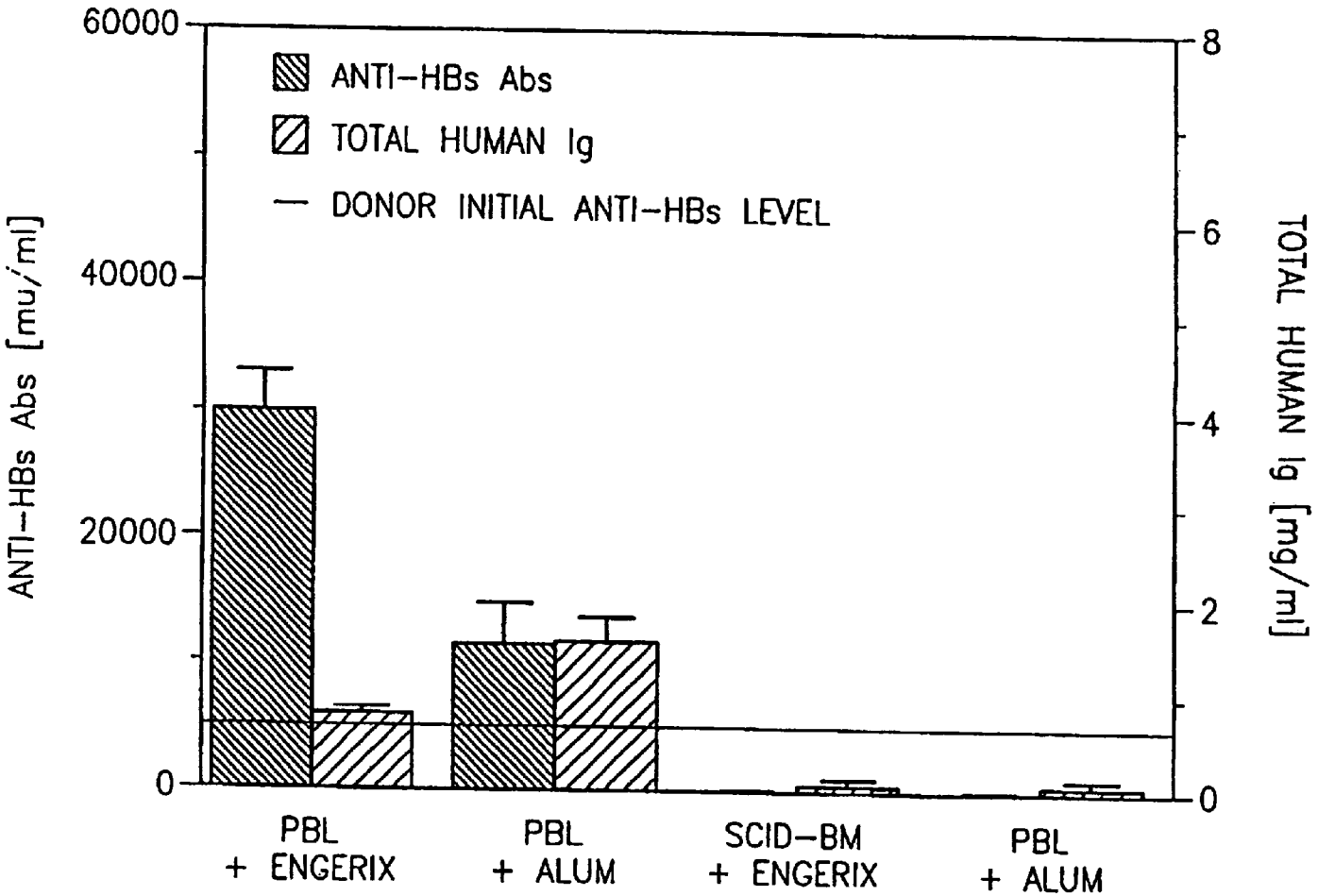
FIG. 1 is a graphic representation showing the amount of total human Ig (mg/ml) and the amount of specific anti HBs antibodies (mU/ml) in the sera of irradiated mice which were radioprotected with SCID bone marrow (chimeric mice). PBL+ENGERIX: the chimeric mice were further transplanted with human PBL from donors positive for anti HBs antibodies, and vaccinated with ENGERIX B in an aluminum hydroxide adjuvant (alum).

Human peripheral blood lymphocytes (PBL) from donors positive for anti HBs antibodies were implanted intraperitoneally into irradiated BALB/C mice which were radioprotected by transplantation of bone marrow from SCID mice. These chimeric mice were immunized with Hepatitis B vaccine (Engerix B) to include a secondary immune response. The production of specific anti HBs antibodies along with total human Ig secretion was measured in mice sera. FIG. 1 shows levels of total human Ig and specific anti HBs antibodies in mice sera 14 days after transplantation of human PBL. Although the levels of human Ig secreted are similar in immunized and control mice, a strong specific immune response develops in mice vaccinated with hepatitis B vaccine as compared to the control group. Comparison of the levels of specific human antibodies produced in response to the antigen in immunized mice to their levels in the donors sera, indicates a 5–10 fold increase in the mice. Moreover, the specific activity measured in mice sera, i.e. the levels of anti HBs specific antibodies per mg of human Ig secreted, is 102–104 fold higher than the specific activity observed in the donor. This increase demonstrates a very high amplification of anti HBs antibody production in response to the antigen in the chimeric mice (FIG. 2). Production of human antibodies is detectable 10 days after immunization and reaches a plateau after three weeks. The specific activity is high at day 13 after immunization and decreases thereafter (due to increase in total human Ig secretion) (FIG. 3).

Example 2

Preparation and Characterization of Human Monoclonal Antibodies Against HBs

Human B cells harvested from mice spleens two weeks after immunization were fused to human-mouse heteromyeloma cells (Posner et al. Supra). Hybridoma cells were tested for their growth rate, total Ig secretion and specific antibody production. Control fusion experiments were performed on the donor PBL that were activated in vitro with PWM and HBVsAg. Fusion frequencies in different experiments range from $0.9–5\times10^{-5}$. Most of the growing hybridoma clones secrete human Ig of which 0.1–4% produce specific human anti HBs antibodies. Anti-HBs secreting hybridoma cells derived from chimeric mice spleens were compared to those obtained from fusion of the donors in vitro activated PBL in terms of Ig type and stability as seen in Table 1 below. The majority of the hybridomas from chimeric mice were found to be IgG type and all were stable for more than 12 months. In contrast, hybridomas derived from donor PBL were mostly unstable, only one clone has been stable for more than 12 months. Two stable hybridoma clones that secrete specific human anti HBs monoclonal antibodies were characterized. As seen in Table 2 below, these antibodies were purified on a protein A column as well as on an anti human Ig-agarose column and were both found to be of IgG1 subclass. Affinity constants range from $1.3\times10^{-9}$ M to $6\times10^{-9}$ M as tested by competitive ELISA. Specificity was tested by competitive inhibition assay using HB surface antigen of the ad-ay (1:1) subtype (FIG. 4). FIG. 5 shows specific binding of the human MoAbs of the invention to HBV by staining human liver fragments infected with HBV.

The gene encoding the variable region of Ab 19.79.5 was isolated, fully sequenced, and its subgroups and CDRs were determined.

The antibody has a fully human Ig gene sequence as determined by alignment to Genebank sequences and Kabat protein sequences. FIG. 10 shows the nucleotide sequence of the cDNA encoding the light chain of the variable region of Ab 19.79.5 and its corresponding amino acid sequence (Sequence identification nos. 1 and 3). FIG. 11 shows the nucleotide sequence of the cDNA encoding the heavy chain of the variable region of Ab 19.79.5 and its corresponding amino acid sequence (Sequence identification nos. 2 and 4).

The sequencing data reveled that the variable region of Ab 19.79.5 consists of the subgroups $V_{H3}$, $J_{H2}$, $V_{\lambda3}$ and $J_{\lambda3}$.

HBV genomes are classified into six groups A to F, based on the degree of similarity in their nucleotide sequences. The genetic variability of HBV is further reflected in the occurrence of different scrotypes of HBsAg. The common determinant 'a' and two pairs of mutually exclusive determinants 'd/y' and 'w/r' enable the distinction of four major subtypes of HBsAg: adw, adr, ayw and ayr. Additional determinants designated subdeterminants of w (w1 to w4) have allowed the definition of our serotypes of ayw (ayw1–4) and two serotypes of adw, i.e. adw2 and adw4. Additional subtype variation is added by the q determinant, which is present on almost all subtypes. Its absence is marked by a 'q-' sign.

The kind of HBV serotypes recognized by Ab 19.79.5 was examined using a set of 15 different HBsAg types (Norder et al., 1992, Journal of General Virology, 73, 3141; Magnius and Norder, 1995, Intervirology, 38, 24–34). As can be seen in FIG. 6, Ab 19.79.5 has a complex recognition pattern of the different HBsAg serotypes.

Example 3

Biological Activity of Human Monoclonal Antibodies Against HBs

The biological activity of Ab 19.79.5 and Ab 18.5.1013 was characterized using the following HBV animal model: a mouse was treated so as to allow the stable engraftment of human liver fragments. The treatment included intensive irradiation followed by transplantation of acid (severe combined immunodeficient) mice bone marrow. Viral infection of human liver fragments was performed ex-vivo using HBV positive human serum (EP 699 235).

The animal model was used in three different modes representing various potential uses of the antibodies: inhibition of infection mode, combined prophylaxis/inhibition mode and combined inhibition/treatment.

1. Inhibition Mode

This model demonstrates the ability to use the antibody to inhibit liver infection by HBV. HBV positive human serum was preincubated with Ab 18.5.1013, followed by standard ex-vivo liver infection. HBV-DNA in mice sera was tested 11 and 18 days after transplantation. As seen in FIG. 7 there was a significant reduction in the percentage of infected animals in the antibody treated group as compared to the untreated group.

2. Combined Prophylaxis/Inhibition Mode

This model represents liver transplantation. In this model mice were treated with Ab 19.79.5(10 I.U./mouse) three days before liver transplantation followed by transplantation of human liver fragments which were ex vivo infected with HBV in the presence of Ab 19.79.5 (100 I.U.). HBV DNA was tested in mice sera 10 and 17 days after transplantation. As can be seen in FIG. 8, there was a significant reduction in the percentage of infected animals in the treated group compared to the control group.

3. Combined Inhibition/Treatment Mode a) HBV positive human serum was preincubated with Ab 19.79.5 followed by standard ex vivo liver infection. b) Mice were treated with Ab 19.79.5 at days 0 and 7 past transplantation. HBV DNA in mice sera was tested on days 11 and 19. As can be seen in FIG. 9, the percentage of infected animals in the Ab 19.79.5 treated group was significantly reduced but rebounded about two weeks after the treatment was stopped.

Example 4

Combination Therapy of Human Monoclonal Antibodies Against HBs and an Anti Viral Agent Using the HBV model described above, mice are treated with an anti viral drug (a nucleoside analogue, 0.5 mg/mouse/day) at days 17–20 post transplantation. A group of mice is further treated with the human monoclonal antibodies of the invention at days 19 and 20. The presence of HBV DNA in mice sera is tested on days 21 and 27.

TABLE 1

| | Anti-HBs Secretors | | Source of Hybridoma |
|---|---|---|---|
| Stability | IgM | IgG | Cells |
| 1 stable for >10 months<br>47 unstable | 25 (52%) | 23 (48%) | In Vitro Activated PBL |
| 6 stable for >10 months<br>3 unstable | 3 (33%) | 6 (67%) | Chimeric Mouse Splenocytes |

TABLE 2

| Kd (M) | Production $\mu g/10^3$ cells/day | Type | Clone |
|---|---|---|---|
| $6.1 \times 10^{-3}$ | 10.3 | IgG1 Vλ | 18.5.1013 |
| $1.62 \times 10^{-3}$ | 5.8 | IgG1 Vλ | 19.79.5 |

SEQUENCE LISTING

```
<160> NUMBER OF SEQ ID NOS: 4

<210> SEQ ID NO 1
<211> LENGTH: 327
<212> TYPE: DNA
<213> ORGANISM: human
<220> FEATURE:
<221> NAME/KEY: CDS
<222> LOCATION: (1)..(327)

<400> SEQUENCE: 1

tcc tat gtg ctg act cag cca ccc tcg gtg tca gtg gcc cca gga aag       48
Ser Tyr Val Leu Thr Gln Pro Pro Ser Val Ser Val Ala Pro Gly Lys
  1               5                  10                  15

acg gcc agg att tcc tgt ggg gga aac aac att gga act aaa aat gtg       96
Thr Ala Arg Ile Ser Cys Gly Gly Asn Asn Ile Gly Thr Lys Asn Val
             20                  25                  30

cac tgg tac cag cag aag cca ggc cag gcc cct gtg ctg gtc gtc tat      144
His Trp Tyr Gln Gln Lys Pro Gly Gln Ala Pro Val Leu Val Val Tyr
         35                  40                  45

gct gat agc gac cgg ccc tca ggg atc cct gag cga ttc tct ggc tcc      192
Ala Asp Ser Asp Arg Pro Ser Gly Ile Pro Glu Arg Phe Ser Gly Ser
     50                  55                  60

aac tct ggg aac acg gcc acc ctg acc atc agc agg gtc gaa gtc ggg      240
Asn Ser Gly Asn Thr Ala Thr Leu Thr Ile Ser Arg Val Glu Val Gly
 65                  70                  75                  80

gat gag gcc gac tat tac tgt cag gtg tgg gat agt gtt agt tat cat      288
Asp Glu Ala Asp Tyr Tyr Cys Gln Val Trp Asp Ser Val Ser Tyr His
                 85                  90                  95

gtg gta ttt ggc gga ggg acc acg ctg acc gtc cta ggt                  327
Val Val Phe Gly Gly Gly Thr Thr Leu Thr Val Leu Gly
            100                 105


<210> SEQ ID NO 2
<211> LENGTH: 109
<212> TYPE: PRT
<213> ORGANISM: human

<400> SEQUENCE: 2
```

-continued

```
Ser Tyr Val Leu Thr Gln Pro Pro Ser Val Ser Val Ala Pro Gly Lys
  1               5                  10                  15

Thr Ala Arg Ile Ser Cys Gly Gly Asn Asn Ile Gly Thr Lys Asn Val
             20                  25                  30

His Trp Tyr Gln Gln Lys Pro Gly Gln Ala Pro Val Leu Val Val Tyr
         35                  40                  45

Ala Asp Ser Asp Arg Pro Ser Gly Ile Pro Glu Arg Phe Ser Gly Ser
     50                  55                  60

Asn Ser Gly Asn Thr Ala Thr Leu Thr Ile Ser Arg Val Glu Val Gly
 65                  70                  75                  80

Asp Glu Ala Asp Tyr Tyr Cys Gln Val Trp Asp Ser Val Ser Tyr His
                 85                  90                  95

Val Val Phe Gly Gly Gly Thr Thr Leu Thr Val Leu Gly
            100                 105


<210> SEQ ID NO 3
<211> LENGTH: 363
<212> TYPE: DNA
<213> ORGANISM: human
<220> FEATURE:
<221> NAME/KEY: CDS
<222> LOCATION: (1)..(363)

<400> SEQUENCE: 3

cag gtg cag ctg gtg gag tct ggg gga ggc gtg gtc cag cct ggg ggg       48
Gln Val Gln Leu Val Glu Ser Gly Gly Gly Val Val Gln Pro Gly Gly
  1               5                  10                  15

tcc ctg aga ctc tcc tgt gca ccg tct gga ttc gtc ttc agg agt tat       96
Ser Leu Arg Leu Ser Cys Ala Pro Ser Gly Phe Val Phe Arg Ser Tyr
             20                  25                  30

ggc atg cac tgg gtc cgc cag act cca ggc aag ggg ctt gag tgg gtg      144
Gly Met His Trp Val Arg Gln Thr Pro Gly Lys Gly Leu Glu Trp Val
         35                  40                  45

tca ctt ata tgg cat gat gga agt aat aga ttc tat gca gac tcc gtg      192
Ser Leu Ile Trp His Asp Gly Ser Asn Arg Phe Tyr Ala Asp Ser Val
     50                  55                  60

aag ggc cga ttc acc atc tcc aga gac aat tcc aag aac aca ttg tat      240
Lys Gly Arg Phe Thr Ile Ser Arg Asp Asn Ser Lys Asn Thr Leu Tyr
 65                  70                  75                  80

ttg caa atg aac agc ctg aga gcc gaa gac acg gct atg tac ttc tgt      288
Leu Gln Met Asn Ser Leu Arg Ala Glu Asp Thr Ala Met Tyr Phe Cys
                 85                  90                  95

gcg aga gag agg ctg att gca gca cct gct gcc ttt gac ctc tgg ggc      336
Ala Arg Glu Arg Leu Ile Ala Ala Pro Ala Ala Phe Asp Leu Trp Gly
            100                 105                 110

cag gga acc ctg gtc acc gtc tcc tcg                                  363
Gln Gly Thr Leu Val Thr Val Ser Ser
        115                 120


<210> SEQ ID NO 4
<211> LENGTH: 121
<212> TYPE: PRT
<213> ORGANISM: human

<400> SEQUENCE: 4

Gln Val Gln Leu Val Glu Ser Gly Gly Gly Val Val Gln Pro Gly Gly
  1               5                  10                  15

Ser Leu Arg Leu Ser Cys Ala Pro Ser Gly Phe Val Phe Arg Ser Tyr
             20                  25                  30

Gly Met His Trp Val Arg Gln Thr Pro Gly Lys Gly Leu Glu Trp Val
```

-continued

```
        35                  40                  45

Ser Leu Ile Trp His Asp Gly Ser Asn Arg Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Met Tyr Phe Cys
                85                  90                  95

Ala Arg Glu Arg Leu Ile Ala Ala Pro Ala Ala Phe Asp Leu Trp Gly
            100                 105                 110

Gln Gly Thr Leu Val Thr Val Ser Ser
        115                 120
```

What is claimed is:

1. A human monoclonal antibody being selected from the group consisting of:

(a) the monoclonal antibody [18.5.103] *18.5.1013* which is secreted by the hybridoma cell line deposited in the European Collection of Cell Cultures (ECACC) under Accession No. 96052170; and (b) fragments of the antibody of (a) which retain the antigen binding [characteristics] *specificity* of the [whole] antibody *of* (*a*).

2. A pharmaceutical composition for reducing the occurrence of HBV infections in a population of individuals by passive immunotherapy and/or for treating HBV infections comprising as active ingredient an antibody in accordance with claim 1 together with a pharmaceutically acceptable carrier.

3. A method for the treatment of HBV infections comprising administering to an individual in need a therapeutically effective amount of a pharmaceutical composition according to claim 2 to treat HBV infection.

4. A method for reducing the occurrence of HBV infections in a population of individuals by passive immunotherapy, comprising administering to a population of individuals a pharmaceutical composition according to claim 2, to reduce the occurrence of HBV infections in the population.

5. A method for the treatment of HBV infections comprising administering to an individual in need a therapeutically effective amount of the antibody of claim 1 to treat HBV infection.

6. A method for reducing the occurrence of HBV infections in a population of individuals by passive immunotherapy, comprising administering to a population of individuals an antibody of claim 1, to reduce the occurrence of HBV infections in the population.

7. A pharmaceutical composition for reducing the occurrence of HBV infections in a population of individuals by passive immunotherapy, and/or for treating HBV infections comprising as an active ingredient at least one antibody in accordance with claim 1 in combination with at least one other active ingredient being an anti viral agent.

8. A pharmaceutical composition according to claim 7 wherein the anti viral agent is selected from the group consisting of: interferons, anti HB polyclonal antibodies, nucleoside analogues and inhibitors of DNA polymerase.

9. A method for the diagnosis of HBV infections in a body fluid sample comprising:

(a) contacting said sample with an antibody of claim 1 under conditions enabling the formation of antibody-antigen complexes; *and*

(b) determining the level of antibody-antigen complexes formed, wherein a determination of the presence of a level of antibody-antigen complexes significantly higher than that formed in a control sample indicates an HBV infection in the tested body fluid sample.

10. A human monoclonal antibody being selected from the group consisting of:

(a) the monoclonal antibody 19.79.5 which is secreted by the hybridoma cell line deposited in the European Collection of Cell Cultures (ECACC) under Accession No. 96052168; and (b) fragments of the antibody of (a) which retain the antigen binding [characteristics] of the [whole] antibody *of* (*a*).

11. The hybridoma cell line deposited at the ECACC on May 22, 1996 under Accession No. 96052170.

12. The hybridoma cell line deposited at the ECACC on May 22, 1996 under Accession No. 96052168.

*13. A pharmaceutical composition for reducing the occurrence of HBV infections in a population of individuals by passive immunotherapy and/or for treating HBV infections comprising as active ingredient an antibody in accordance with claim 10 together with a pharmaceutically acceptable carrier.*

*14. A method for the treatment of HBV infections comprising administering to an individual in need a therapeutically effective amount of a pharmaceutical composition according to claim 13 to treat HBV infection.*

*15. A method for reducing the occurrence of HBV infections in a population of individuals by passive immunotherapy, comprising administering to a population of individuals a pharmaceutical composition according to claim 13, to reduce the occurrence of HBV infections in the population.*

*16. A method for the treatment of HBV infections comprising administering to an individual in need a therapeutically effective amount of the antibody of claim 10 to treat HBV infection.*

*17. A method for reducing the occurrence of HBV infections in a population of individuals by passive immunotherapy, comprising administering to a population of individuals an antibody of claim 10, to reduce the occurrence of HBV infections in the population.*

*18. A pharmaceutical composition for reducing the occurrence of HBV infections in a population of individuals by passive immunotherapy, and/or for treating HBV infections comprising as an active ingredient at least one antibody in accordance with claim 10 in combination with at least one other active ingredient being an anti viral agent.*

*19. A pharmaceutical composition according to claim 18 wherein the anti viral agent is selected from the group consisting of interferons, anti HB polyclonal antibodies, nucleoside analogues and inhibitors of DNA polymerase.*

*20. A method for the diagnosis of HBV infections in a body fluid sample comprising:*

(*a*) *contacting said sample with an antibody of claim 10 under conditions enabling the formation of antibody-antigen complexes; and*

(*b*) *determining the level of antibody-antigen complexes formed, wherein a determination of the presence of a level of antibody-antigen complexes significantly higher than that formed in a control sample indicates an HBV infection in the tested body fluid sample.*

* * * * *